(12) United States Patent
Harty (10) Patent No.: US 9,776,064 B2
(45) Date of Patent: *Oct. 3, 2017

(54) PROTECTIVE TEMPERATURE HELMET AND SHOULDER PADS, PROTECTIVE TEMPERATURE HELMET AND SHOULDER PAD LINER

(71) Applicant: Robert D. Harty, Sycamore, IL (US)

(72) Inventor: Robert D. Harty, Sycamore, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/611,985

(22) Filed: Feb. 2, 2015

(65) Prior Publication Data
US 2016/0345652 A1    Dec. 1, 2016

Related U.S. Application Data

(63) Continuation-in-part of application No. 13/354,202, filed on Jan. 19, 2012, now Pat. No. 8,943,617, which
(Continued)

(51) Int. Cl.
*A41D 13/00* (2006.01)
*A63B 71/12* (2006.01)
*A61B 5/01* (2006.01)
*A63B 71/10* (2006.01)
*A42B 3/12* (2006.01)
*A42B 3/28* (2006.01)
(Continued)

(52) U.S. Cl.
CPC .......... *A63B 71/1291* (2013.01); *A42B 3/121* (2013.01); *A42B 3/285* (2013.01); *A61B 5/01* (2013.01); *A63B 71/10* (2013.01); *A41D 13/0512* (2013.01); *A61B 2562/0276* (2013.01); *A61F 2007/0012* (2013.01)

(58) Field of Classification Search
CPC .... A41D 13/0512; A42B 3/122; A42B 3/127; A42C 5/04; A42C 5/02
USPC ............ 2/468, 413, 414, 171.2, 181, 171.4, 2/181.6, 181.8, 182.1, 182.2, 182.3, 182.7
See application file for complete search history.

(56) References Cited

U.S. PATENT DOCUMENTS 882,686 A * 3/1908 Ireland .................. A42B 3/122
2/413
4,130,902 A   12/1978 Mackenroth et al.
(Continued)

OTHER PUBLICATIONS

HTFx, Inc., RITE-TEMP Medical Products, http://www.ritetempmedical.com/products.shtml (last visited Apr. 13, 2012).

*Primary Examiner* — Tejash Patel
(74) *Attorney, Agent, or Firm* — Cherskov Flaynik & Gurda, LLC (57) ABSTRACT

The invention provides head, neck, chest, and spine logical impact protection and thermal-regulation device having a webbing adapted to encapsulate head and neck, wherein the webbing is composed of a plurality of reversibly deformable substrates that are capable of being cooled or heated; wherein the webbing further provides apertures interspersed between the reversibly deformable substrates to allow fluid exchange between the head, neck, chest, and spine and the regions exterior to the webbing; and a temperature indicator, wherein the temperature indicator measures the temperatures of the body surface underlaying the webbing.

20 Claims, 7 Drawing Sheets

Related U.S. Application Data is a continuation-in-part of application No. 12/982,621, filed on Dec. 30, 2010, now Pat. No. 8,468,613, which is a continuation-in-part of application No. 10/687,162, filed on Oct. 16, 2003, now Pat. No. 7,861,326.

(60) Provisional application No. 61/434,281, filed on Jan. 19, 2011.

(51) Int. Cl.
*A61F 7/00* (2006.01)
*A41D 13/05* (2006.01)

(56) References Cited

U.S. PATENT DOCUMENTS

| | | |
|---|---|---|
| 4,133,055 A | 1/1979 | Zebuhr |
| 4,354,284 A | 10/1982 | Gooding |
| 4,686,710 A * | 8/1987 | Marston ............ A41D 13/0512 2/2.5 |
| 4,854,319 A | 8/1989 | Tobin |
| 6,397,399 B1 | 6/2002 | Lampe et al. |
| 6,557,179 B1 | 5/2003 | Reuven |
| 6,625,820 B1 | 9/2003 | Lampe |
| 6,678,896 B2 | 1/2004 | Robinson et al. |
| 7,028,344 B2 | 4/2006 | Toth |
| 8,262,601 B2 | 9/2012 | Cumming et al. |
| 8,943,617 B2 * | 2/2015 | Harty ................. A42B 3/121 2/468 |
| 2002/0100109 A1 * | 8/2002 | Hoop ................. A41D 13/0512 2/425 |

\* cited by examiner

FIG. 1

BASE OF NECK

PROTECTIVE TEMPERATURE HELMET AND SHOULDER PADS, PROTECTIVE TEMPERATURE HELMET AND SHOULDER PAD LINER

CROSS REFERENCE TO RELATED APPLICATIONS

The instant application claims priority as a continuation in part of U.S. patent application Ser. No. 13/354,202, filed on Jan. 19, 2012, issued as U.S. Pat. No. 8,943,617 on Feb. 3, 2015.

U.S. patent application Ser. No. 13/354,202 claimed priority both as a non-provisional application of U.S. Provisional Patent Application Ser. No. 61/434,281 filed on Jan. 19, 2011, currently expired, and also as a continuation in part of U.S. patent application Ser. No. 12/982,621, filed on Dec. 30, 2010, issued as U.S. Pat. No. 8,468,613 on Jun. 25, 2013, the entirety of which is incorporated by reference, which in turn is a continuation in part application to U.S. patent application Ser. No. 10/687,162, filed on Oct. 16, 2003, issued as U.S. Pat. No. 7,861,326 on Jan. 4, 2011.

BACKGROUND OF THE INVENTION

1. Field of the Invention

This invention relates to a shock absorbing helmet liner which simultaneously keeps the wearer's head and neck and spine cool or warm while providing an indication of the temperature of the wearer's head and neck and chest and abdomen and spine, and more specifically, this invention relates to a device for regulating body temperature, for example by cooling the brain, reducing swelling on the brain, reducing the effects of hyperthermia, heat stroke, fever, while simultaneously preventing concussion injuries.

2. Background of the Invention

A majority of concussions sustained by persons involved in contact sports are the result not only of hard blows, but also from poor designs of the helmets and helmet liners. Temperatures within all existing helmets and helmets liners can be in excess 130° F.-140° F.

The inventor's contention is that a leading contributor to concussions is heat. The brain, when subjected to sustained temperatures above 98.6° F., can start to swell. This is why the majority of the percentage of heat leaving the body in hyperthermia situations exits through the head, given its large vascularization.

There is only enough room between the brain and the cranium for an additional 10 cubic centimeters of fluid or mass. That fluid space is easily taken up in high heat situations (such as what may occur during sustained physical exertion), either due to brain swelling, or brain bleeding, which can also be the result of high heat scenarios.

In such scenarios, the brain may potentially move closer to the cranium or actually make contact the cranium, This makes the player incredibly prone to concussion inasmuch as the 10 cc of cushioning space mentioned supra is gone.

A need exists in the art for a device to cool the brain and upper spine while simultaneously protecting the brain from blows to the head. Additionally, there is a need to remotely and rapidly determine the temperatures that a wearer's head, neck, and spine are experiencing during physical activity. These three functions should be integrally molded into one feature of the device. The device should be worn alone, or else adapted to be worn with standard helmets or headgear so as to removably receive the headgear. An embodiment of the device would be integrally molded with a helmet such that the device may be worn as a stand-alone protective device. Finally, an embodiment of the device should be usable without a helmet.

SUMMARY OF INVENTION

An object of the invention is to provide a device for reducing concussions that overcomes many of the disadvantages of the prior art.

Another object of the invention is to provide a device for reducing concussions to overheated players. A feature of the invention is the use of cooling substrates in conjunction with standard protective headgear. An advantage of the invention is that the substrates simultaneously serve to cool the brain and spine and cushion the brain from external blows to the head.

Yet another object of the present invention is to provide a means for preventing brain swelling due to heat. A feature of the invention is the use of a plurality of cooling substrates received in regions of a helmet liner and or helmet. An advantage of invention is that the helmet liner is removably received by the overlying helmet. Another advantage is that the substrates can be separated from the helmet liner for prior refrigeration, or the substrates can remain in the helmet liner such that the entire liner can be refrigerated. The invented device also is adapted to being heated, to accommodate instances where the head requires heating.

Still another object of the present invention is to provide a combination head protection, head thermal-regulation device. A feature of the device is a stand alone, homogeneously constructed, shock-absorbing webbing adapted to be cooled or heated. An embodiment of the webbing includes means for receiving cooled or heated fluids while another embodiment is heated or cooled directly, without the need for first being filled with cooled or heated fluids. An advantage of the device is that no additional head protection is necessary, thereby conferring light weight, thermal management to the wearer's head, while also eliminating the physical shock associated with a rigid over-layment, such as a helmet, in instances of impact. The reversibly deformable, stand alone embodiment provides soft crumple zones to eliminate the aforementioned physical shock.

Another object of the present invention is to provide a combination head and upper body cushioning and thermal regulation device. A feature of the device is a stand alone, homogenously constructed, shock absorbing webbing adapted to be cooled or heated. An embodiment of the webbing includes means for receiving cooled or heated fluids while another embodiment is heated or cooled directly, without the need for first being filled with cooled or heated fluids, inasmuch as individual compartments comprising the webbing are prefilled with fluid. An advantage of the device is that no additional protection to the head, chest, shoulders, and upper spine is necessary, thereby conferring light weight, thermal management to the wear's upper body while also eliminating the physical shock associated with a rigid over-layment, such as a helmet and shoulder pads, in instances of impact.

Yet another object of the present invention is to provide a means for indicating temperature around a wearer's head to rapidly determine risk of brain swelling due to heat. A feature of the invention is the use of a temperature indicator in thermal communication with the wearer's body (e.g. head). An advantage of the device is that the temperature indicator can rapidly indicate that the wearer is in danger of overheating (e.g. brain swelling and concussion).

The invention provides a head cooling/heating device comprising a webbing adapted to encapsulate the human head; and a plurality of cavities defined by said webbing, said cavities adapted to reversibly receive a plurality of substrates, wherein the substrates are capable of being cooled or heated.

The present invention still further provides a head and neck impact protection and thermal-regulation device comprising a webbing adapted to encapsulate the human head and neck; a plurality of cavities defined by said webbing, said cavities adapted to reversibly receive a plurality of reversibly deformable substrates, wherein the substrates are capable of being cooled or heated; wherein the webbing further defines apertures interspersed between the cavities to allow fluid exchange between the head and neck and the regions exterior to the webbing; and a temperature indicator reversibly attached to, or integrally molded with the webbing wherein the temperature measures the temperatures of the body surface covered by the webbing.

The invention also provides a head and neck impact protection and thermal-regulation device comprising; a webbing adapted to encapsulate the head and neck, wherein the webbing comprises a plurality of reversibly deformable substrates that are capable of being cooled or heated; wherein the webbing further comprises apertures interspersed between the reversibly deformable substrates to allow fluid exchange between the head and neck and the regions exterior to the webbing; and a temperature indicator, wherein the temperature indicator measures the temperatures of the body surface underlaying the webbing.

The invention moreover provides an upper-body impact protection and thermal-regulation device comprising a webbing adapted to encapsulate the human head and neck, wherein downwardly depending webbing extends from the base of the neck to overlay the human back, chest, and shoulders; a plurality of cavities defined by said webbing, said cavities adapted to reversibly receive a plurality of reversibly deformable substrates, wherein the substrates are capable of being cooled or heated; and wherein the webbing further defines apertures interspersed between the cavities to allow fluid exchange between the head and neck and the regions exterior to the webbing.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a device for both cooling and protecting and cushioning the brain, both functions occurring simultaneously. Starting with a webbing akin to a loosely fitting swimming cap, the device also comprises material to cover the rear base of the skull and the cervical spine such that substantially all seven of the cervical vertebra are overlaid by the device.

An embodiment of the invention further comprises a temperature indicator reversibly attached to, or integrally molded with, the webbing overlaying the rear of the skull such that the temperature indicator displays the temperature of the air around the user's head while the device is worn.

An embodiment of the invention further comprises laterally positioned substrate situated on both sides of the neck. This laterally positioned substrate, when the device is worn, extends from the rear base of the skull to front of the neck. This laterally positioned substrate facilitates cooling of the lateral portions of the neck and particularly the carotid arteries found in the neck. Optionally, this embodiment includes downwardly depending substrate to overlay the cervical vertebrae of the user. This downwardly depending substrate provides a means to prevent a depending end of a helmet from digging into the cervical spine in instances of whiplash. Additional downwardly depending substrate can be added to this embodiment to overlay the chest, shoulders and spine descending downward to as low as to cover the entire lumbar region of the spine, but not limited to same. This additional downwardly depending substrate provides protection to sensitive areas of the torso such as the thoracic and lumbar regions of the spine, the heart, the sternum, the clavicles, the shoulders, and the brachial arteries.

Another embodiment of the invention comprises a stand-alone helmet defining a two layer configuration. A first outer layer overlays a second layer and is more rigid, less rigid, or equally as pliable compared to the second layer. For example, an outer layer may be comprised of thermoplastic urethane (i.e., TPU cushioning). The second layer is either integrally molded to the first layer or else removably attached to the first layer. The second layer is adapted to receive cooled or heated free flowing fluid or else individual packets of cooled or heated fluid.

Figure 1:
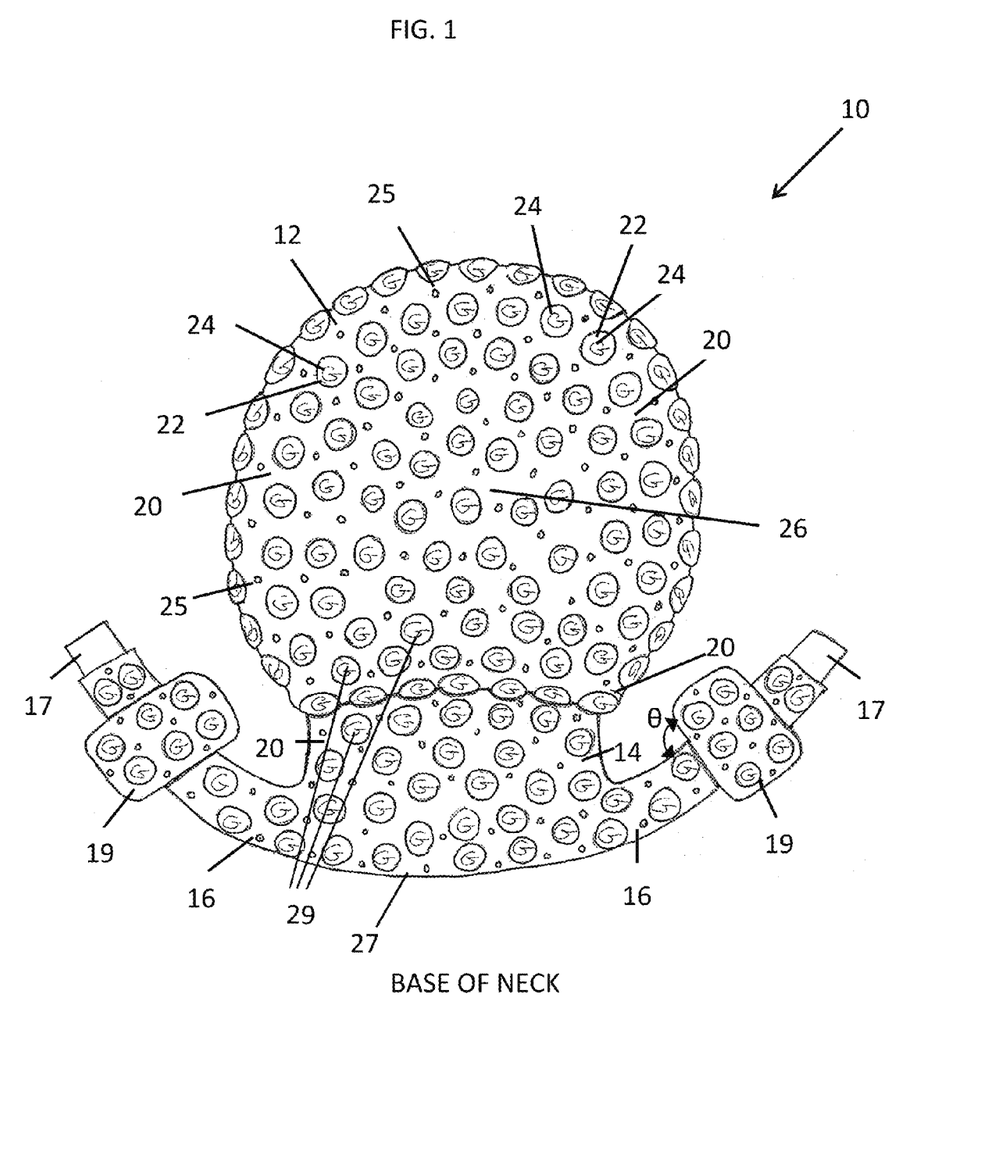
FIG. 1 is a plan view of a helmet liner, in accordance with features of the present invention.

FIG. 1 is a plan view of an embodiment of the invention, the device designated as numeral 10. Generally, the device 10 comprises three regions, a head cap region 12, a cervical cap region 14, and a carotid cap region 16. These three regions may be removably attached to each other, or integrally molded to each other. In the later iteration, a webbing 20 is used, the webbing defining individual pockets 22 adapted to removably receive cushioning substrates 24. Not all portions of the webbing need to be loaded with the cushioning substrates. For example, in one envisioned use, the top portion 26 of the webbing, which would overlay the trailing frontal and leading parietal portions of the skull, would not contain the cushioning substrates 24 while webbing overlying the trailing (i.e. dorsal) parietal region and the occipital and temporal regions of the skull would contain the cushioning substrate 24. This configuration may be beneficial for cyclists and other athletes more prone to whiplash, but less prone to intense physical contact from other players.

In another embodiment, the webbing covering all portions of the skull (i.e., frontal, parietal, occipital, temporal, sphenoid, and even the zygomatic and mandible regions) would be outfitted with cushioning substrates 24. Not only would overlying of the entire skull provide all encompassing shock protection thereto, but the temperature of the cushioning substrates 24 overlying the entire skull would optimize temperature regulation.

The webbing can define a myriad of different substrates. In one embodiment, as depicted in FIG. 1, portions of the webbing are continuous, while other portions define transversely extending apertures or vents 25. These vents provide a means for facilitating air exchange from areas between the head and the liner, and to areas outside or exterior of the liner. The vents 25 are shown dispersed throughout the webbing so as to be positioned over substantially all regions of the skull. However, the vents 25 can be relegated to specific regions of the cap such that all the vents are positioned over only selected regions of the skull, such as the parietal region, or the occipital region, or the temporal region or the frontal region of the skull, or the vents are positioned over a plurality of these regions but not all of the regions of the skull.

In another embodiment, cushioning substrates 24 define the webbing 20 without the use of pockets 22. In this embodiment, the webbing 20 is formed by integrally molding together a plurality of cushioning substrates 24 instead of placing the substrates in pockets. With the cushioning substrates defining the webbing without pockets, the webbing can comprise more cushioning substrates per unit area, thereby also increasing the impact cushioning and temperature regulation ability per unit area. As with the embodiment depicted in FIG. 1, portions of the webbing in this embodiment may define transversely extending apertures or vents 25.

Figure 2:
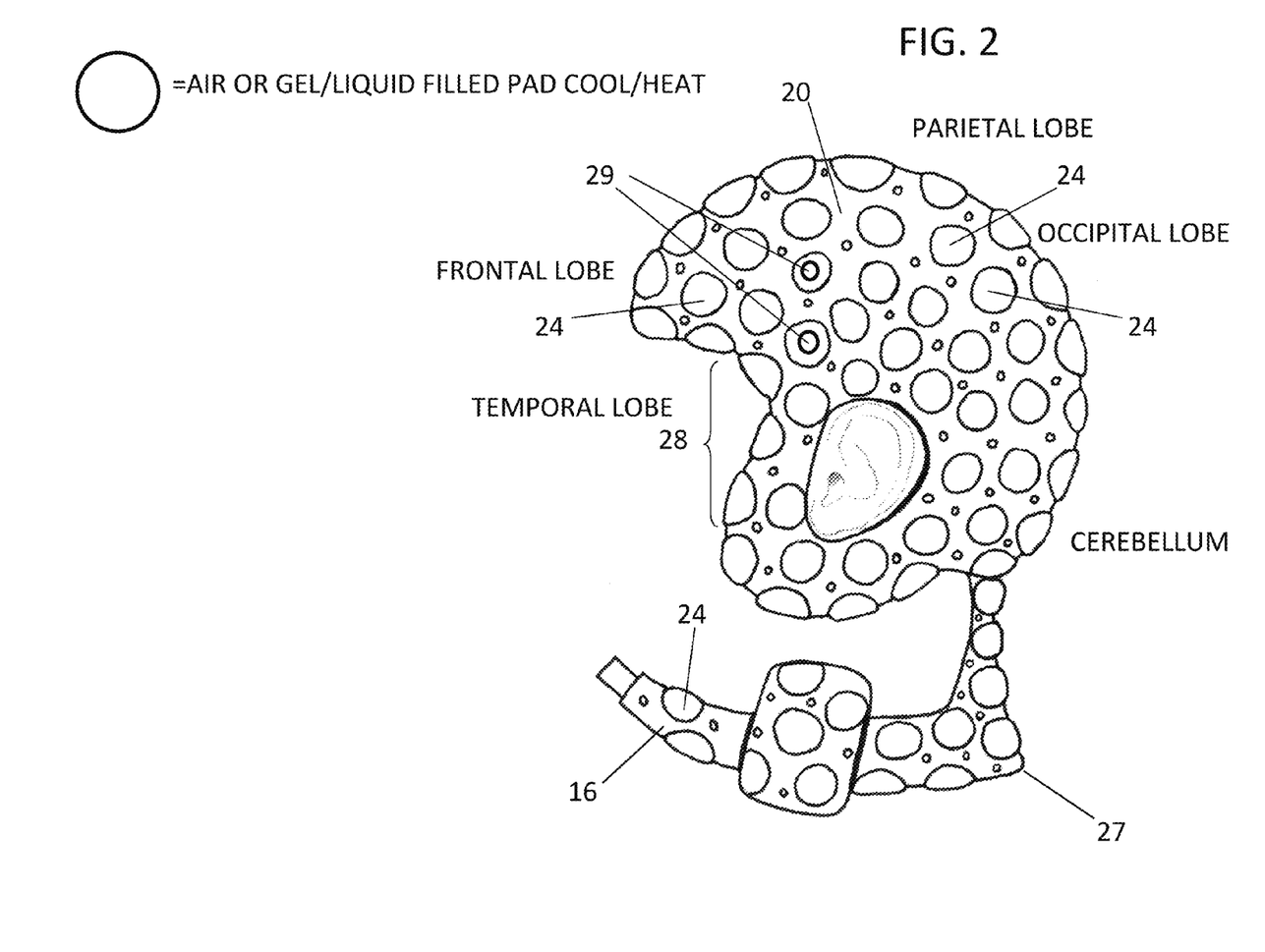
FIG. 2 is an elevated view of the invented helmet liner, in accordance with features of the present invention.

FIG. 2 is a side view of an embodiment of the invention in which all regions of the webbing contain the cushioning substrates 24. However, and as with vent placement, the cushioning substrates alternatively are positioned to cover only specific regions of the skull. The device also is adapted to receive cushioning substrates such that some of the substrates are at a temperature different than other cushioning substrates. This allows areas of the skull to be cooled, while other areas of the skull to not be cooled (or cooled to a similar extent), while other areas may be heated.

Figure 3:
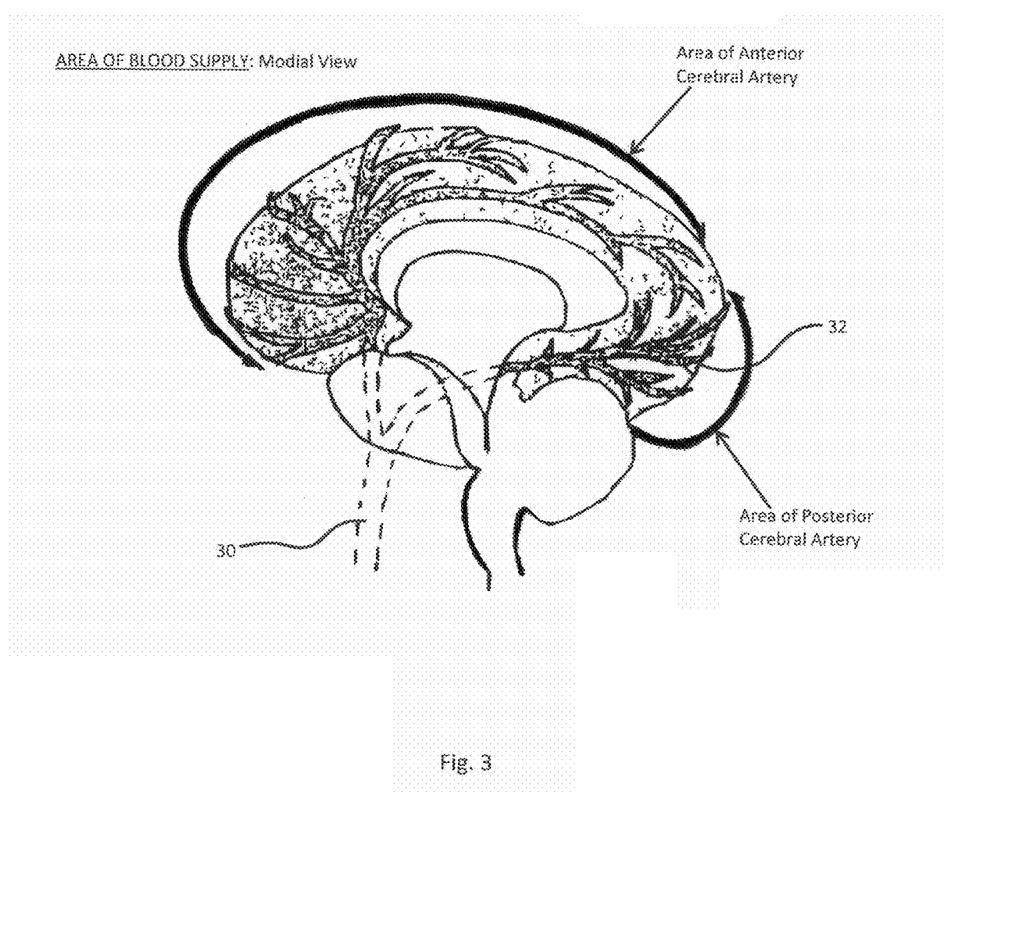
FIG. 3 is diagram showing blood flow through the head.

The invention allows placement of the cushioning substrate at strategic blood flow routes of the head. FIG. 3 is a view of the blood supply routes in the human brain. It is envisioned that cushioning substrate 24, preheated or precooled, are most effective when placed directly opposite these routes. For example, a plurality of chilled cushioning substrates 24 positioned along the temporal region 28 of the webbing would cool blood supplied by the carotid artery. Or, a plurality of chilled cushioning substrates 24 positioned along the base of the skull, so as to contact the occipital regions of the skull, would cool blood flowing through the posterior cerebral artery 32.

An embodiment of the invention includes one or more straps for contacting the medial and anterior portions of the wearer's neck. As shown in FIG. 1, two straps 16 are shown, with a means for attaching the distal ends 17 of the strap together at the front (anterior) of the neck. Also as shown in FIG. 1 are substrates 19 in slidable communication with the straps 16 and along the longitudinal axis of the straps. As such, a means for effecting this sliding communication is a slit in an outer membrane of the substrates, and parallel to the longitudinal axis of these substrates 19 adapted to slidably receive longitudinally extending portions of the straps. The longitudinal axis of these slidable substrates 19 are positioned at an angle theta to the longitudinal axis of the straps. As such, the angle theta (between about 0 and 90 degrees) provides a means for allowing the slidable substrate to confer additional cooling or heating treatment to areas beyond the periphery of the straps 16.

The cushioning substrates 24 may comprise a plurality of reversibly deformable substrates, such as plastic conduits or sacs, which may receive any suitable fluid such as air (for cushioning), a heated fluid (such as heated gas or heated liquid), a cooled fluid (such as cooled gas or cooled liquid), or a combination of such fluid phases and temperatures. Exemplary gaseous fluids include, but are not limited to, air, nitrogen, noble gases, and a combination of these. Exemplary liquid fluids include, but are not limited to, water, vegetable oil, mineral oil, liquid-solid combinations such as water-based deformable low density gel compositions, plasticizers with a plurality of particulates dispersed therein, deformable gel compositions comprising carbopol and water/glycerin, emulsions, and combinations of these substances.

Additionally, the cushioning substrates 24 are protective of any area of the body that they overlay in the instant invention. The substrates are protective in that they provide cushioning from collision by absorbing force that would otherwise transfer fully and directly to the body of a user of the instant invention.

Figure 4:
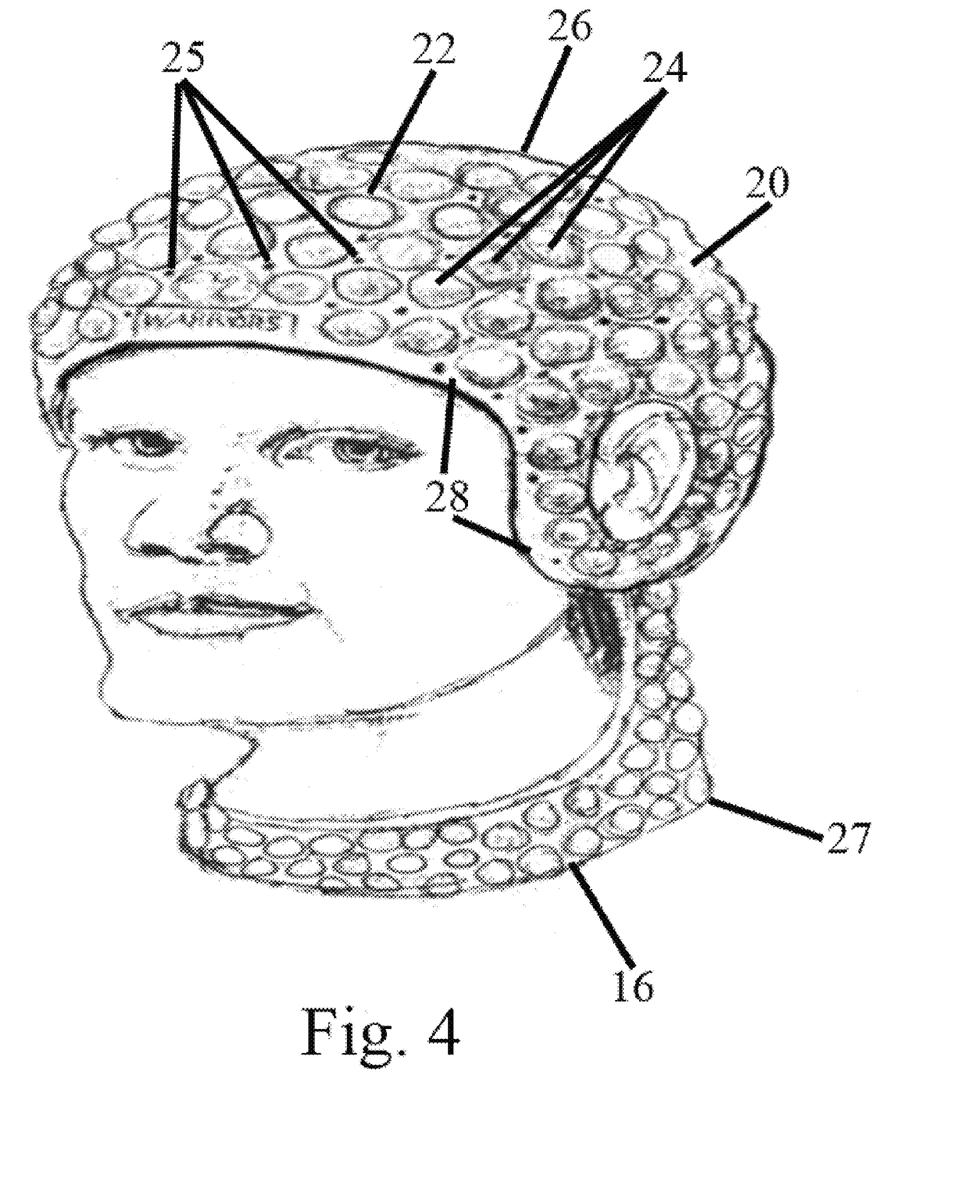
FIG. 4 is perspective view of an embodiment of the invention worn by a use, in accordance with features of the present invention.

FIG. 4 is a perspective view of an embodiment of the device in operation. This embodiment is shown being worn alone, i.e., without a helmet. It is noteworthy that a depending end 27 the embodiment extends at least to the base of the cervical spine, and as shown, slightly below the seventh vertebra.

To increase protection to the wearer, the cap is adapted to reversibly receive a semi-rigid, rigid, substrate such as a standard football helmet, cyclist helmet, baseball cap, or other typical sports head protective gear. The semi-rigid, rigid substrate may alternatively be integrally molded to the cap. Such sports head protective gear would substantially overlay the device. The semi-rigid or rigid substrate may also be low friction. Alternatively, a plastic/fiberglass/metal cap can be reversibly attached to this embodiment. This heterogeneously constructed (i.e. hybrid) embodiment not only would this confer rigid protection to the wearer, but it will also minimize friction if contact is made with another person.

Figure 5:
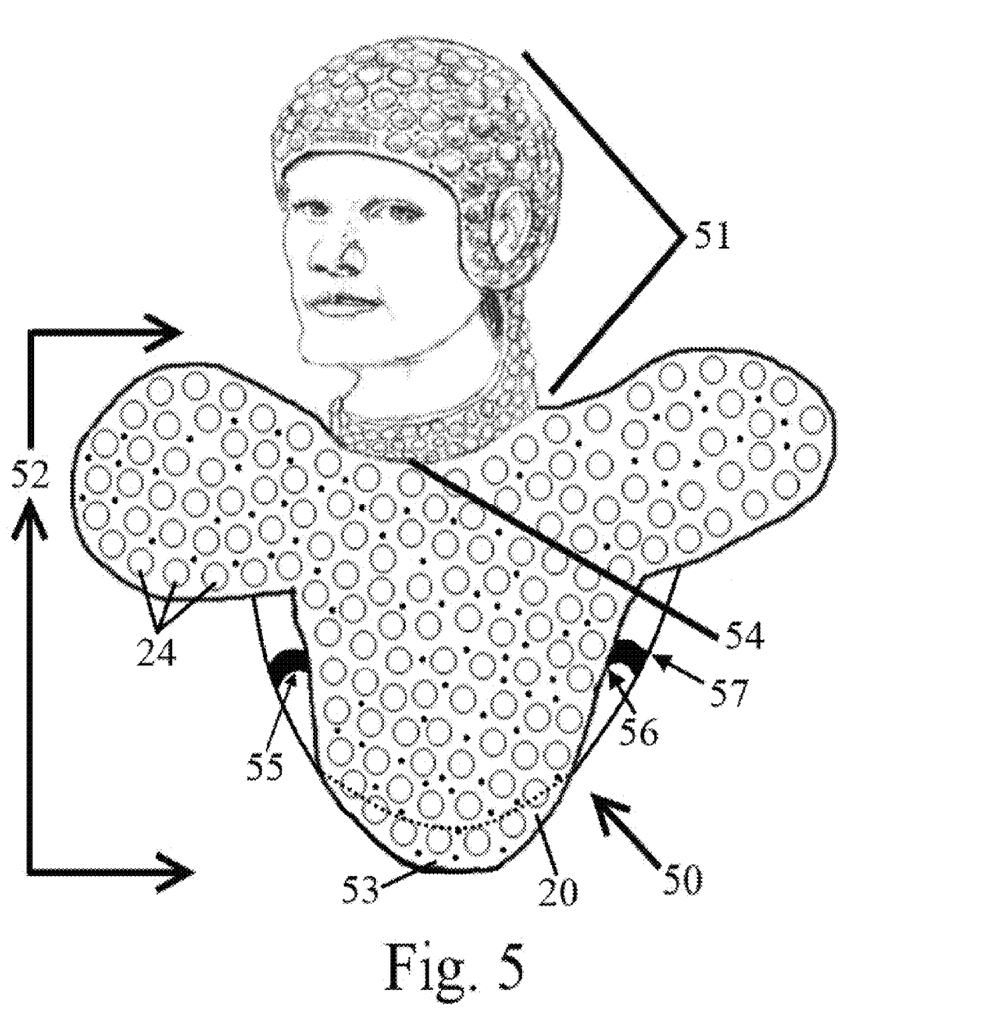
FIG. 5 is a perspective view of an embodiment of the invention worn by a user, in accordance with features of the present invention.

FIG. 5 is a perspective view of an embodiment of the invention in operation, the device designated as numeral 50. This embodiment is shown being worn alone, i.e. without shoulder pads or a helmet which may otherwise overlay it. Generally, the device 50 comprises two regions, a head/neck region 51 and an upper body region 52. A depending end 53 of the upper body region may extend downwardly to define an abdominal protection cushioning region. The regions may be removably attached to each other, or integrally molded to each other. The upper body region 52 in this embodiment comprises downwardly depending webbing 20 that extends from the base of the neck 54 of the head/neck region 51 to the bottom of the sternum on the anterior side to the base of the scapulae on the posterior side with webbing positioned to overlay both shoulders.

Optionally, the downwardly depending webbing can extend down to the waist line on the anterior side and to the bottom of the lumbar region of the spine on the posterior side. The webbing 20 covering a user's chest, back, and shoulders containing cushioning substrates 24, would provide for cushioning against blows to critical, sensitive areas of the torso such as the thoracic and lumbar regions of the spine, the heart, the sternum the clavicles, the shoulders, and the brachial arteries. Additionally, with the temperature regulation of the cushioning substrates 24 overlaying the back, chest, and shoulders of a user allows for optimal temperature regulation of the upper body.

To increase protection to the wearer, the downwardly depending webbing that covers the chest and spine can be fixed in place to prevent displacement of the cushioning substrates caused by the movement of a user of the device. The downwardly depending webbing can be fixed in place by including one or more straps 55 that connect the webbing overlaying a user's chest with the webbing overlaying the user's spine. Alternatively, or in addition thereto, straps are provided depending from the depending end 53 of the webbing so as to attach to the pants, belt or belt loop of the wearer.

The straps 55 can comprise a number of different configurations that allow for applying tension between the connecting the webbing overlaying a user's chest with the webbing overlaying the user's spine. An exemplary configuration is a pair of elastic straps having first ends 56 and second ends 57 wherein the first ends 56 are affixed to the webbing overlaying a user's chest a point of the longitudinal axis of the downwardly depending webbing. The second ends 57 are affixed to the webbing overlaying the user's spine at the same point of the longitudinal axis of the downwardly depending webbing such that, when worn, the elastic strap provides tension substantially perpendicular to the longitudinal axis of the downwardly depending webbing. The tension applied by the strap 55 prevents the downwardly depending webbing from shifting. Additionally, the straps can comprise a more rigid material and a device to adjust tension to allow for a user of the device to select the tension said straps.

To moreover increase protection to the wearer, the downwardly depending webbing is adapted to reversibly receive a semi-rigid or rigid substrate such as standard football shoulder pads. The semi-rigid, rigid substrate may alternatively be integrally molded to the downwardly depending webbing. Such shoulder pads would substantially overlay the downwardly depending webbing of the device. The semi-rigid or rigid substrate may also be low friction. Alternatively, a plastic/fiberglass/metal covering can be reversibly attached to the downwardly depending webbing in this embodiment. This heterogeneously constructed (i.e. hybrid) embodiment not only would confer rigid protection to the wearer, but it will also minimize friction if contact is made with another person.

Figure 6:
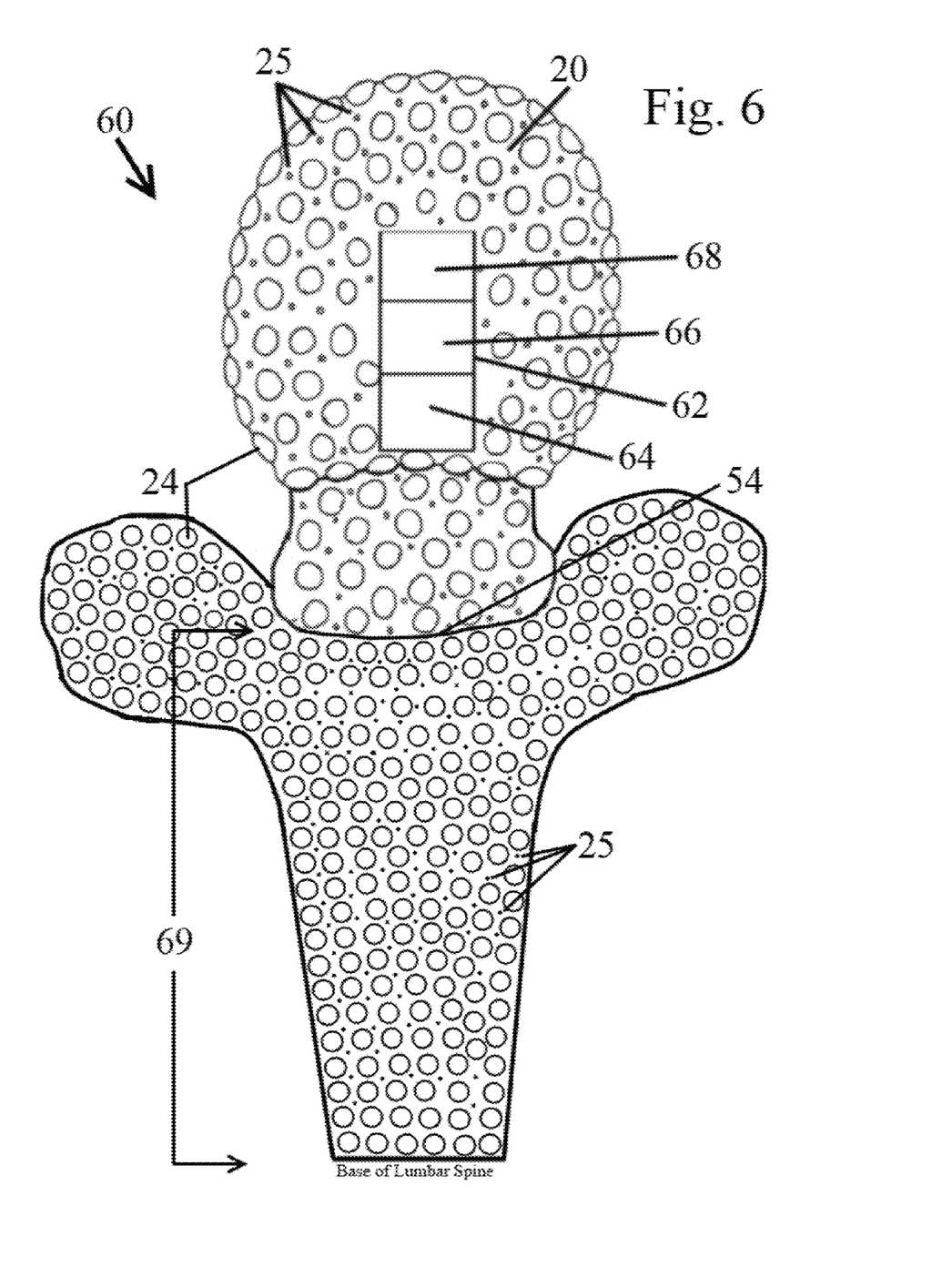
FIG. 6 is a back surface view of an embodiment of the invention, in accordance with features of the present invention.

FIG. 6 is a back surface view of an embodiment of the invention, the device designated as numeral 60. In this embodiment, a temperature indicator 62 is reversibly attached to a portion of the webbing 20 over a plurality of vents 25, or alternatively reversibly received by an individual pocket 22 of the webbing, such that the temperature indicator 62 is in fluid contact with the head of a user when the device is worn. Alternatively, the temperature indicator is irreversibly attached to the webbing, for example painted on, glued on, or integrally molded with the webbing. Cushioning substrates which overlay the temperature sensitive body regions of the user can be filled with fluid that changes color with changing temperature.

To measure the risk in real time of swelling on the brain, concussion, hyperthermia, heat stroke, and fever while a user is active and wearing the device, the temperature indicator actively and continuously measures the temperature of the region of the body underlying the temperature indicator. The risk for the user experiencing these heat-related conditions can then be assessed by observing the temperature readings given by the temperature indicator.

An embodiment of the temperature indicating module is depicted in FIG. 6, wherein the temperature indicator 62 is divided into thirds, a lower third 64, a middle third 66, and an upper third 68. With the temperature indicator 62 measuring the vapor and air temperature around the head of the user, in one embodiment, the temperature indicator 62 visually indicates the temperature of the fluid surrounding the wearer's head thereby minimizing the risk of concussion due to brain swelling is immediately estimated either by the wearer, or by monitoring personnel viewing the wearer from a large distance.

Aside from visually indicating temperature changes, in one embodiment, the invention incorporates electronic sensors for notifying the wearer or monitoring personnel of temperature changes. In this embodiment, a temperature probe is in electrical communication with the temperature indicator 62. The temperature indicator further includes a rechargeable power source, storage memory, wireless communications antenna, and an embedded controller. In one embodiment, the embedded controller collects readings from the temperature probe, stores them in storage memory, and transmits via the wireless communications antenna at regular intervals. In one embodiment, the wireless antenna and controller includes logic to facilitate communications using wireless protocols including WIFI, Bluetooth, low power Bluetooth, and direct communication using the industrial, scientific, and medical radio bands.

In another embodiment, the embedded controller of the temperature indicator 62 also includes a local wireless connection to a heart rate monitor worn by the user of the protective device. In this embodiment, the wireless transmissions from the controller include both any readings from the temperature probe, but also from the heart rate monitor. The frequency of the readings from the temperature probe are increased if the heart rate of the wearer spikes, in this embodiment.

The readings, including temperature and pulse information, are stored in the storage memory and transmitted by the embedded controller depending on availability of receiving units. In one embodiment, multiple protective devices 60 are used at one time, and the embedded controllers in each device communicate with one another exchanging data in a local ad-hock network, using the lowest energy transmission method possible, switching to a more energy demanding protocol only as the signal from a player attenuates. In this embodiment, one embedded controller acts as the 'team captain' and collects all information about team mates and transmits them to a receiving station by the coaching staff on the side line. In this embodiment, only one team member's device uses the high-power demanding WIFI connection, while the information exchanges between all remaining team mates occur using a much less demanding transmission standard, such as low power Bluetooth or direct serial wireless communications.

Figure 7:
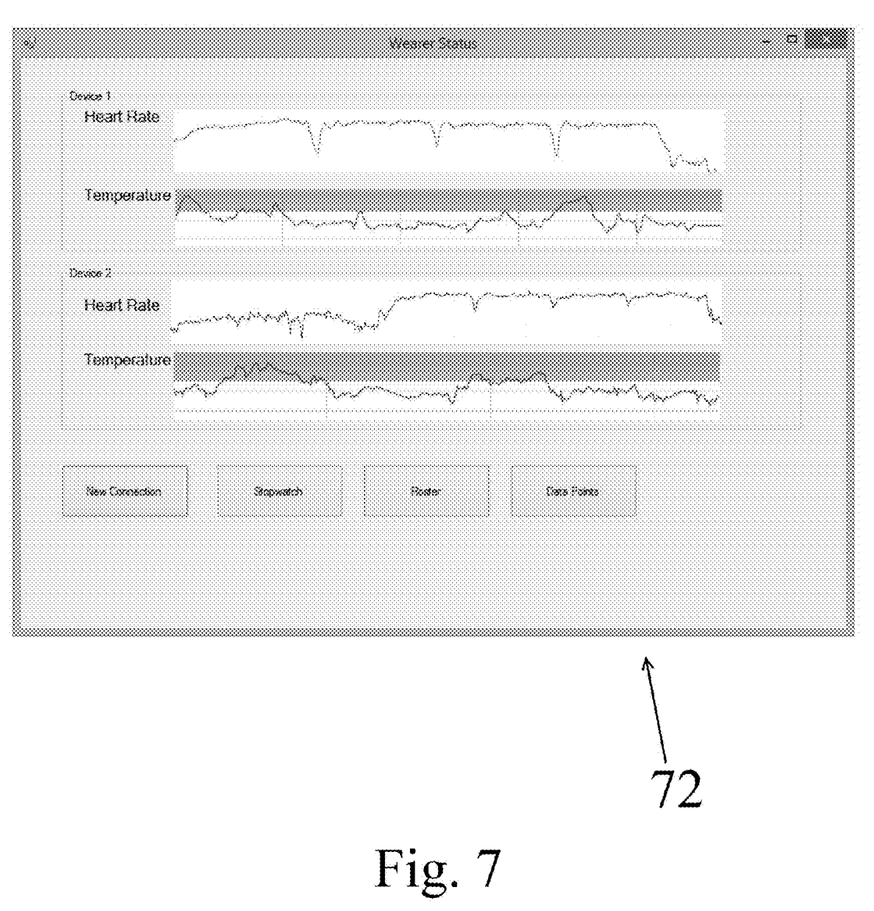
FIG. 7 is a sample interface screen of computer program that displays temperature readings taken of a user, in accordance with the features of the present invention.

The transmissions are received by the support staff at regular intervals, as determined by the embedded controller and are displayed to the support staff using an interface on a standard computing device such as a tablet, phone, or computer. A sample interface screen 72 is depicted in FIG. 7.

Returning to FIG. 6, in this exemplary embodiment, each of the thirds of the temperature indicator 62 changes color when the fluid surrounding a user's head is within a specified range. For example, the bottom third 64 would be green at a range of temperatures from about 70° F. to about 98° F. The middle third 66 would be yellow at a range of temperatures from about 98° F. to about 105° F. The upper third 68 would be red at a range of temperatures from about 105° F. to about 140° F. In this embodiment, the bottom third 64 showing green indicates that the wearer is at normal concussion risk, the middle third 66 showing yellow indicates that wearer may be nearing overheating and may need a rest, and the upper third 68 showing red indicates that the user is overheating and needs to cease activity for risk of concussion or other heat related conditions.

The temperature indicator may comprise a number of different devices that can indicate the temperature experienced by a user's head. In the example depicted by FIG. 6, the temperature indicator can be a liquid crystal thermometer using thermocrhomic crystals. Additional examples include an electronic, digital thermometer programmed to display specified colors in specified temperature ranges, or make specified sounds in specified temperature ranges. Or, the temperature indicator can be an electronic thermometer that displays the temperature of the fluid surrounding a user's head while wearing the device either on the thermometer itself or on a device wirelessly receiving temperature readings from the temperature indicator. Also, the temperature indicator can be a temperature sensitive paint applied to the exterior of the webbing that fluoresces specified colors in specified temperature ranges.

Alternatively, a remotely situated probe positioned between the user's skin and the underside of the webbing provides a temperature reading, that reading subsequently displayed on a three region panel.

The temperature indicator may be powered by any portable power source such as batteries or solar cells. Some power sources for the temperature indicator are rechargeable either by removing the power source and recharging it or charging the power source while it resides in the temperature indicator.

As depicted in FIG. 6, downwardly depending webbing can extend from the base of the neck 54 to overlay the length of the spine down to and including the lumbar region 69.

It is to be understood that the above description is intended to be illustrative, and not restrictive. For example, all of the substrates, either the underlying liner, the stand alone embodiment, or the hybrid embodiments, are adapted to receive reflective material or printed material. Generally, the above-described embodiments (and/or aspects thereof) may be used in combination with each other. In addition, many modifications may be made to adapt a particular situation or material to the teachings of the invention without departing from its scope. For example, instead of a solid, one-piece helmet overlying the cooling/heating cap, or one-piece shoulder pads overlying webbing on the upper body, a single rigid or semi-rigid material such as a disk 29 is attached or otherwise substantially overlays each of the single gel cushioning substrates 24, or a substantial number of the gel cushioning substrates in a predetermined area of the device. These single disks can either be removably attached (e.g., via a hook and pile attachment arrangement), or else permanently attached to their respective gel elements 24, either via adhesive, or integrally molded together. In the case of the disks being removably attached, this confers the ability for the user to personalize her headliner by selecting various colored disks.

Aside from being disk-shaped, the single substrates attached to a single gel element 24 can define a myriad of substantially two dimensional shapes, including squares, polygonals, and also three-dimensional shapes such as cubes, pyramids, or interlocking materials such that adjacent substrates matingly receive each other. Alternatively, these single substrates can vary in size and shape for use on the same device. These single substrates can be comprised of metal, plastic, glass, ceramic, fiberglass, carbon fiber composite, and combinations of these materials. Methods of production of these single substrates include 3-D printing, extrusion, drop forge, or solgel processing. These single substrates, as well as the constituents of other embodiments of the invention, can be thermally conductive, radio translucent, electrically insulative, water proof, or a combination of these features.

The single disk to gel pad configuration confers additional impact protection, just as a standard helmet and shoulder pads do, but also allows for direct air exchange from the wearer-contact surface of the device, through the apertures 25, to the atmosphere. This disk-to-gel cushion configuration defines a flexible helmet and shoulder pads with the advantages of typical helmets and shoulder pads and the advantages of full air exchange.

While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A head and neck impact protection and thermal-regulation device comprising:
   a. a webbing adapted to encapsulate head and neck, wherein the webbing comprises a plurality of reversibly deformable substrates that are capable of being cooled or heated;
   b. wherein the webbing further comprises apertures interspersed between the reversibly deformable substrates to allow fluid exchange between the head and neck and the regions exterior to the webbing; and
   c. a temperature indicator, wherein the temperature indicator measures the temperatures of the body surface underlaying the webbing.

2. The device as recited in claim 1 further comprising downwardly depending webbing that extends from the base of the neck to overlay the back, chest, and shoulders of a wearer.

3. The device as recited in claim 1 wherein the temperature indicator further comprises a device selected from the group consisting of a liquid crystal thermometer, temperature sensitive paint, a digital thermometer, a digital thermometer programmed to display specified colors in specified temperature ranges, a digital thermometer programmed to emit specified sounds in specified ranges, a digital thermometer that transmits temperature readings to a receiving device, and combinations thereof.

4. The device as recited in claim 1 wherein the webbing further defines flexible sheeting defining cavities adapted to reversibly receive the deformable substrates.

5. The device as recited in claim 4 wherein the substrates are cooled or heated while residing in the cavities.

6. The device as recited in claim 4 wherein the substrate are cooled or heated before being received by the cavities.

7. The device as recited in claim 1 wherein at least one of the deformable substrates is the temperature indicator.

8. The device as recited in claim 1 further comprising a semi-rigid or rigid material overlaying the webbing.

9. The device as recited in claim 8 wherein the material is reversibly attached to the webbing.

10. The device as recited in claim 8 wherein the material is integrally molded with the webbing.

11. The device as recited in claim 1 wherein the device is adapted to receive a helmet.

12. An upper-body impact protection and thermal-regulation device comprising:
    a. a webbing adapted to encapsulate the human head and neck, wherein downwardly depending webbing extends from the base of the neck to overlay a wearer's back, chest, and shoulders, the webbing comprising a plurality of reversibly deformable substrates, wherein the substrates are capable of being cooled or heated; and
    b. wherein the webbing further defines apertures interspersed between the cavities to allow fluid exchange between the head and neck and the regions exterior to the webbing.

13. The device of claim 12 further comprising a temperature indicator, wherein the temperature indicator measures the temperatures of the body surface underlaying the webbing.

14. The device as recited in claim 13 wherein the temperature indicator further comprises a device selected from the group consisting of a liquid crystal thermometer, temperature sensitive paint, a digital thermometer, a digital thermometer programmed to display specified colors in specified temperature ranges, a digital thermometer programmed to emit specified sounds in specified ranges, a digital thermometer that transmits temperature readings to a receiving device, and combinations thereof.

15. The device as recited in claim 12 wherein the downwardly depending webbing extends to the waist line of the wearer on the anterior side and to the base of the lumbar region of the spine on the posterior side.

16. The device as recited in claim 15 wherein the webbing is adapted to cool or heat the cervical, thoracic, and lumbar regions of the spine.

17. The device as recited in claim 12 wherein the webbing further comprises flexible sheeting defining pockets adapted to reversibly receive the deformable substrates.

18. The device as recited in claim 12 wherein the device is adapted to receive a helmet and shoulder pads.

19. The device as recited in claim 12 wherein the substrates provide impact resistance to the head, neck, shoulders, and chest.

20. The device as recited in claim 12 further comprising a semi-rigid or rigid material overlaying the webbing.

* * * * *